United States Patent [19]

Rollwitz

[11] Patent Number: 4,701,705

[45] Date of Patent: Oct. 20, 1987

[54] NMR MOISTURE MEASUREMENTS

[75] Inventor: William L. Rollwitz, San Antonio, Tex.

[73] Assignee: Southwest Research Institute, San Antonio, Tex.

[21] Appl. No.: 558,770

[22] Filed: Dec. 5, 1983

[51] Int. Cl.$^4$ .......................................... G01R 33/20
[52] U.S. Cl. ................................. 324/306; 324/308; 324/307
[58] Field of Search ............... 324/300, 306, 308, 313, 324/65 R, 310; 73/73, 861.04, 861.08, 861.11, 861.12, 861.13, 861.14, 861.15, 861.16, 861.17

[56] References Cited

U.S. PATENT DOCUMENTS

| | | | |
|---|---|---|---|
| 2,999,977 | 9/1961 | Brown | 324/322 |
| 3,045,175 | 7/1962 | Rollwitz | 324/313 |
| 3,068,398 | 12/1962 | Shoolery | 324/310 |
| 3,529,234 | 9/1970 | Keen | 324/300 |
| 3,621,379 | 11/1971 | Watson et al. | 324/318 |
| 3,691,455 | 9/1972 | Moisio | 324/307 |
| 4,240,028 | 12/1980 | Davis, Jr. | 73/73 |
| 4,390,957 | 6/1983 | Skarlos | 324/300 |

Primary Examiner—Jerry W. Myracle
Assistant Examiner—Scott M. Oldham
Attorney, Agent, or Firm—Gunn, Lee & Jackson

[57] ABSTRACT

In the preferred and illustrated embodiments hereof, a method and apparatus for conducting NMR moisture measurements is set forth. In various forms, hydrogen transient NMR signal peak amplitude values indicative of total hydrogen concentration of the tested material space. The hydrogen concentration is converted by a constant into water concentration. In one embodiment, a comparison is made between the NMR peak voltage of the unknown material and the NMR peak voltage from a standard sample having a specified water content to obtain a calibration for determining moisture content as a weight percentage in the tested specimen. If the densities of the two samples vary, the weights of each are necessary for accurate measurements. An alternative procedure involves determining moisture and material from the hydrogen in the water and in the material itself. In this procedure, the spin-spin relaxation $T_2$ for the moisture is preferably more than three times longer than the $T_2$ for the hydrogen in the solid or substrate hygroscopic material. Subsequently, two separate measurements can be obtained at separate times and their proportion is related to the percent water. An alternate procedure is used when the $T_2$ of the water varies as a function of the percentage of water. In that instance, the values proportional to the total hydrogen in the sample and to the hydrogen in the water must be obtained at the same time so that the ratio is proportional to the percent water independent of the variations in $T_2$. In the last two procedures, weight measurement is not required.

22 Claims, 5 Drawing Figures

SEMILOG GRAPH OF NMR SIGNALS

NMR SIGNAL FOR COAL SAMPLES

SEMILOG GRAPH OF
MAGNETIZATION CHANGES

NMR RATIO FOR
COAL SAMPLES

NMR MOISTURE MEASUREMENTS

BACKGROUND OF THE DISCLOSURE

This disclosure is directed to a method and apparatus for detection of the percent moisture in a sample. It is particularly adapted to use with flowing materials. In like fashion, it can be used with non-flowing batches. The present invention is directed to a transient NMR test apparatus which includes a coil which interrogates or tests a specified or definite "detection volume." This term refers to the volumetric space within a coil (an RF coil) which is interrogated or tested for resonant response. For instance, a typical configuration involves a pipe, a flat belt or a V-belt, for conducting a flow of some product through the radio frequency magnetic field of the transient NMR detection coil. The coil has a specified volumetric capacity. The detection volume is that portion of material in the pipe; namely, a cylindrical plug within the RF coil and exposed to the requisite steady magnetic field perpendicular to the RF field. The coil is conventionally would as a cylinder, defining a circular cross-section. It is possible to use the entire cross-section such as a filled pipe, or to use less than the entire cross-section as in the instance of a flat belt conveyer passing through the RF coil. The maximum detection volume is thus geometrically configured dependent on the shape and size of the RF detection coil normally positioned around the cooperative pipe. The term "pipe" refers to a tubular member formed of a material permitting magnetic flux and RF field lines to be formed through the pipe. The pipe should be made from non-conducting materials such as plastic or glass. It is not possible too use conductors and ferrous materials because they will not pass the radio frequency field. If a conductive pipe must be used, the detection coil can be mounted inside of the pipe. This also applies to various types of conveyer belts.

The detection volume is that volume within the physically constrained coil and magnetic field described above. Ordinarily, the present invention is applied to a pipe or other type of conduit which is conducting a flowing material. Flow velocities may ordinarily vary widely. Even with a high flow velocity, such as 300 feet per minute, the test which is contemplated herein is accomplished so rapidly that the portion of flowing material within the detection volume is substantially stationary during testing. The flowing material is pumped through the pipe, passing through a magnetic field transverse to the flow. The magnetic field provides polarization of the element of interest. Hydrogen is the element of interest for measurement of water concentration. Periodically, a pulsed RF magnetic field at right angles to the polarizing magnetic field is transmitted from the coil. The pulse has a duration measured in microseconds. If the pulse has a duration of three microseconds, and if the return signal from the NMR interrogation has been completed within 20 microseconds, then the flowing material during the entire 20 microsecond interval moves approximately 0.001 inches at approximately 300 feet per minute. If the interval is 100 microseconds, the movement will be about 0.005 inches. As will be understood, this small movement does not particularly distort the data obtained from the pulsed NMR interrogation.

The present invention may be utilized for measurement of flowing materials wherein the material is formed of hydrogen containing compounds. It also operates successfully where there are no hydrogen compounds. For instance, an important measurement is the moisture content in flowing cement. Cement is a compound essentially free of hydrogen. Therefore, one may safely assume any hydrogen measured in the flowing cement is part of the moisture. An alternate situation is the measurement of moisture in flowing food products such as flour or corn starch. Such food products are primarily hydrocarbons and have various hydrogen compounds in their make-up. Another situation where moisture measurement is in a flow of a material which has been wetted by oil and water or absorbed the oil and water. The oil can be treated as a part of the material undergoing testing and hence the measurement of the percent moisture is analogous to the measurement of water in hydrocarbons material. The oil can be measured separately when the water is treated as part of the material being tested.

Many mixes and variations between the material and the moisture in the material can be imagined. The categories described above are representative of such variations. In the several categories, suitable measurements are obtained whereby the moisture content can be indicated.

An important feature of this disclosure is the ability of the method and apparatus to measure the moisture content without weighing the material. It is inconvenient to rapidly get the weight of a batch of material. This typically requires more time for the scales to settle than the time required to obtain the NMR test data taught by this disclosure. Even worse, there is far greater difficulty in obtaining the weight of a flowing mass. For instance, particulate material such as cement, flour, foodstuffs and the like flow through a pipe in quantities or at rates which vary somewhat. The weight cannot be presumed. It is relatively difficult to measure weight of a flowing material. The present invention avoids the separate measurement of weight. Separate weight measurement is avoided by using an NMR voltage proportional to the total weight of the sensed sample. Another NMR voltage is obtained from the same transient NMR signal which is directly proportional to the weight of water. The ratio of the last voltage to the first (times a constant) gives the water concentration without weighing. Accordingly, data is then obtained indicative of percent concentration of water independent of weight measurement. In a first embodiment of the present invention, the material of interest in which moisture is measured in a material which does not include hydrogen as an element of the material. One example is flowing cement, primarily calcium carbonate.

An alternate embodiment is concerned with the measurement of moisture in materials, where the material itself is a compound which includes hydrogen. Food such as flour, starch, and hydrocarbon products exemplify this category. Another example is cellulose materials such as paper, wood or plants which hold water. Not only is there hydrogen in the cellulose material making up the paper, hydrogen is also in water; the water may be different phases. In very low percentage moisture content, the water very tightly bonded in a crystalline phase. Where there is more water, it is less tightly bonded in an amorphous phase. Higher concentration of loosely bonded water are typically found in capillary spaces in the fiber structure of the paper.

Another embodiment of this invention involves detecting moisture content in a sample wherein oil is also in the sample. In other words, there are tow different liquids present. This invention is best able to separate the transient NMR response of the two liquids provided the relaxation times of the hydrogen in the two liquids are different by approximately threefold or more. This difference provides adequate signal discrimination. The separation is easier with a larger difference. If reduced accuracy is acceptable, it is practicable to work with a twofold difference in $T_2$. From the foregoing, it will be observed that a variety of materials falling within the broad definitions set forth in exemplary fashion can be measured and tested to determine moisture content as a percentage. While the absolute measurement of the water is seldom used, the preferred presentation is the voltage ratio percentage approach since variations of density and temperature are removed.

This invention may therefore be adapted for use with a flowing stream of materials in the general categories described above. The output can be obtained periodically. For instance, a new moisture measurement can be obtained once per second. The rate at which the data can be obtained usually exceeds the rate at which the date is normally required. A single transient NMR interrogation of the present invention is able to be completed in microsecond speed. Briefly, the flowing material in the pipe is directed through a magnetic field. The magnetic field polarizes the hydrogen nuclei. The flowing material also passes through a coil forming a field, namely an RF field. An interrogation radio frequency pulse is transmitted into the RF coil. A short pulse is sufficient, typically in the range of a few microseconds. A received transient NMR pulse signal encodes the data of interest, the onset of the received NMR signal measured from transmission of the interrogation pulse, being as short as 50 microseconds. Depending on scale, the time after transmission may be longer. A large number of data points can be obtained, but excessive data points are usually not needed because the flowing material does not move very fast between pulses. While the NMR duration material is moving, the rate of speed is usually so slow relative to the transient duration there is usually no benefit from obtaining a large number of data points other than improving the signal to noise ratio. The foregoing sets forth the general nature of this invention and features thereof. The description set forth below directed to the preferred embodiments is best understood in conjunction with the drawings.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
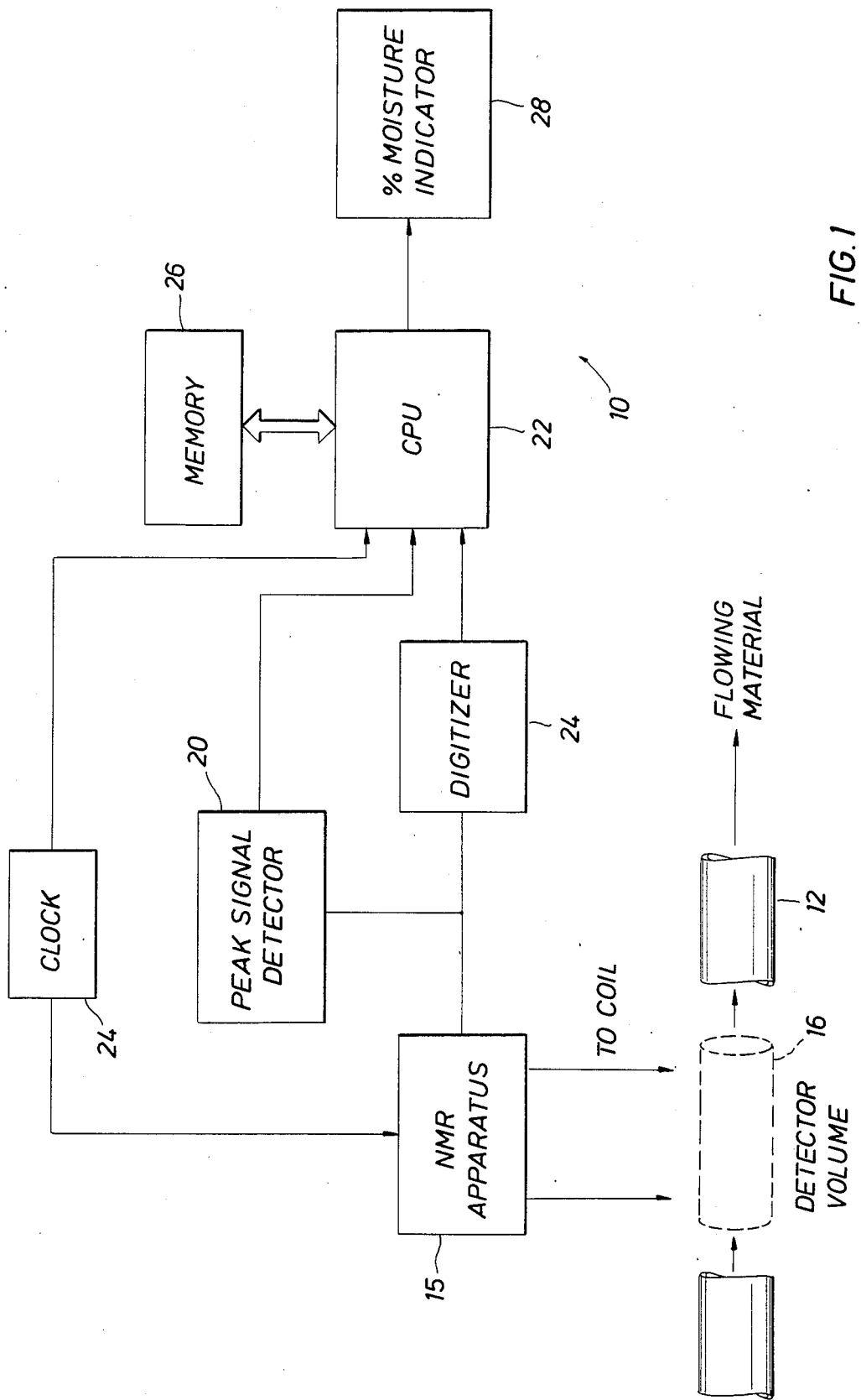
FIG. 1 is a schematic block drawing of an apparatus suitable for determination of a percent of moisture in a flowing material.

Attention is first directed to FIG. 1 of the drawings. There, an NMR detection apparatus is identified generally by the numeral 10. The apparatus cooperates with a pipe 12 or other belt or conveyer system. A flowing material passes along the pipe. In the near vicinity of the NMR apparatus 15, a magnet (not shown) forms fairly uniform field lines across the path of the flowing material in the conduit of pipe 12. In this vicinity, the pipe is preferably made of non-magnetic material. Rather, a material is chosen which does not interrupt the magnetic lines. This eliminates ferrous materials. Alternate materials include aluminum or plastic materials. There is a detector volume at 16. It is defined by the size of the detection coil and cooperative magnet (not shown). In conformance with conventional transient NMR operation, the detection coil forms radio frequency magnetic field lines perpendicular to the magnetic lines formed by the magnet. The magnet can be of any arrangement so long as it produces the flux lines in the proper direction in the conduit or conveyer 12. The coil is formed of N turns concentric around the pipe 12. The coil defines the detection volume on the interior of the pipe or pathway of flowing product. The detector volume 16 is the maximum volume of material exposed to the lines of flux of the magnet and also to the field lines (formed by the coil) of suitable strength. That is, the detector volume 16 is the volume in which the flowing material may be located and which is sufficiently irradiated to yield an NMR response. In the present disclosure, the term detector volume thus refers to the volume which is tested for transient NMR response. It is a volume within the RF magnetic field formed by the coil which is potentially filled with flowing material. The degree of filling or fill factor may vary, the detector volume defining the maximum volume for receipt of the flowing material.

A pulse is transmitted to the coil from the NMR apparatus 15 and an output is formed which is the transient NMR response. Attention is momentarily directed to FIG. 2 of the drawings which shows one such response. There, the ordinate is the transient NMR response measured in volts. Several curves have been incorporated. The curves are shown to extend out through about 50 microseconds, it being recognized that a peak first occurs (at about 5 to 7 microseconds on the graph) and decay is thereafter noted. The numeral 16 identifies a low moisture coal response. This curve is typically obtained from a low moisture coal. The curve 17 is obtained from a coal of moderate moisture content while the curve 18 is obtained from a relatively high moisture content.

Returning now to FIG. 1, it will be observed that the NMR apparatus 15 forms an output signal which is applied to a peak signal detector 20. The peak signal detector and the output signal are both input to a CPU 22. The output signal is first passed through a digitizer 24 which converts the analog signal into a series of digital words. The entire system runs under operation of a clock 24. The CPU collaborates with a memory 26, and periodically forms an output which is an indication of the percent moisture. The indicator 28 provides data suitable for use. The data is typically expressed in the form of a percentage moisture content. Scaling by different factors can be also accommodated.

Figure 2:
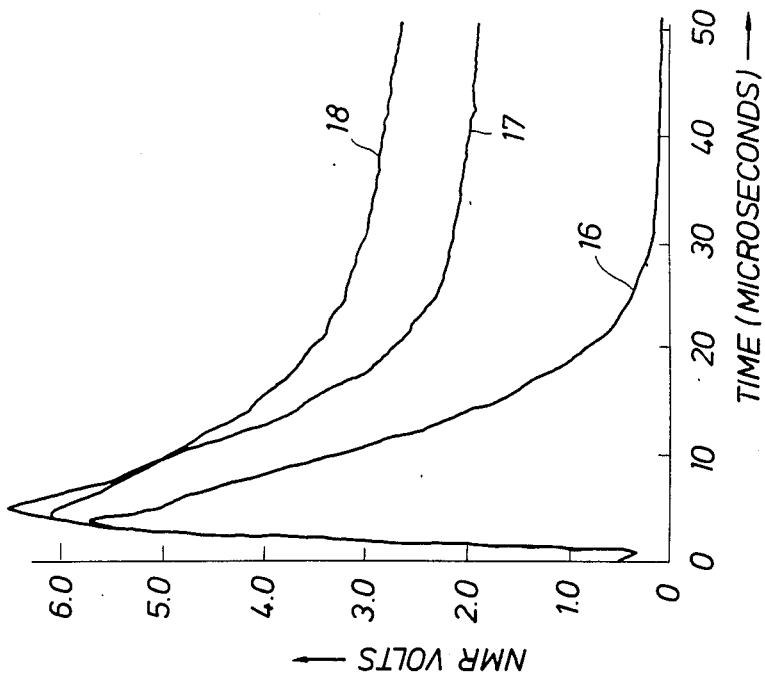
FIG. 2 is a graph of the transient NMR signal obtained from various samples as a function of time.

The data presented in FIG. 2 is typical of the NMR response obtained from coal. Other materials will provide responses of a similar nature.

The first procedure to be described is concerned with obtaining a percent moisture measurement of a flowing material typically characterized as hygroscopic. Examples of such material without hydrogen are calcium, chloride or zinc chloride. In fact, such a material can act as a dessiccant, attracting, absorbing and holding water. It is assumed in this instance that the flowing hygroscopic material does not incorporate a compound of hydrogen. As a first step, the detection volume is filled with the flowing material of a known density with a known water content. An NMR peak output voltage is obtained from this.

A sample having an unknown moisture content is introduced into the detector volume. For the sample, an NMR voltage is also obtained. The peak voltage is representative (proportional) of the number of hydrogen nuclei or the weight of hydrogen in the detector volume which, on multiplication by suitable constants, becomes the weight of water in the detector volume. This value enables subsequent comparison with a standard to determine the percentage moisture in weight percent. One technique of converting this value into percent weight is set forth in U.S. Pat. No. 3,045,175 of the present inventor. This yields the percent moisture from the line width of the NMR signal which is inversely proportional to the relaxation time.

An alternative procedure to utilize the NMR response to determine moisture in a material is dependent on the spin-spin relaxation time $T_2$. There is a characteristic $T_2$ for hydrogen in the water absorbed on the material. That will be identified as the relaxation time $T_{2w}$. If $T_2$ of the sample is more than three times longer and preferably five times longer than the comparable relaxation time of the solid (identified as $T_{2s}$), then a contrast can be obtained. This contrast is observed in the two widely separated relaxation time components of the NMR signal $T_{2s}$ and $T_{2w}$. Alternatively, it is also shown in the FID NMR response signal. Shown in FIGS. 2 and 3, either the FID signal in FIG. 2 or the $T_2$ characteristic of the NMR response signal in FIG. 3 can be used to obtain appropriate voltages for isolation to yield the percent moisture content by weight without weight measurement on multiplication by suitable constants.

Figure 3:
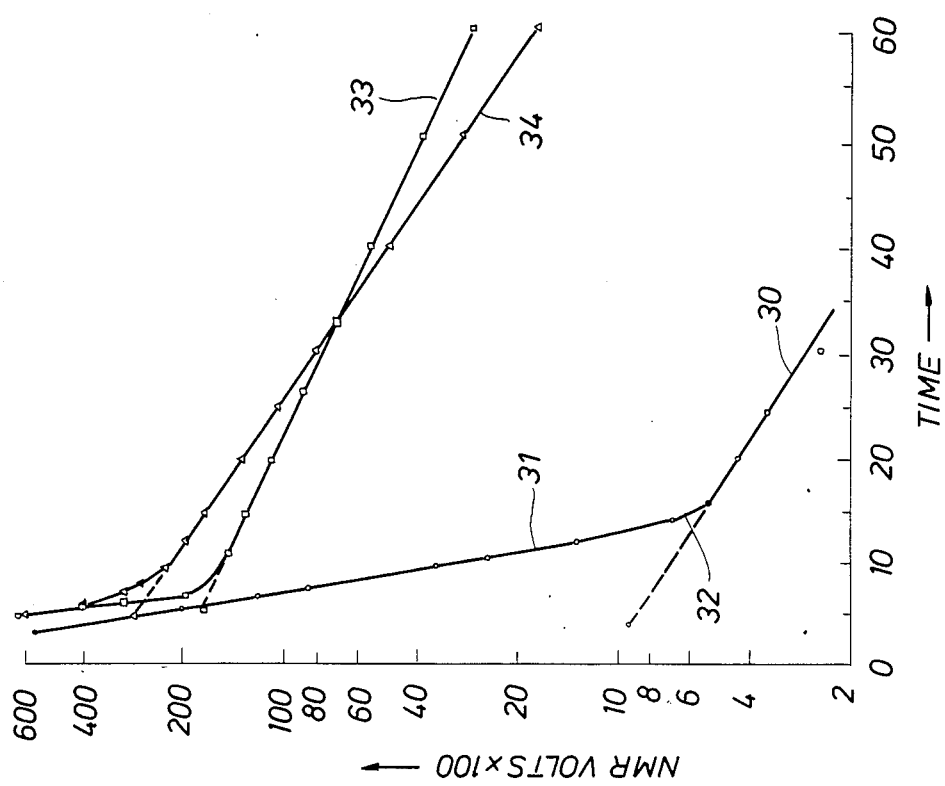
FIG. 3 is a graph of the transient NMR response plotted on a semilog ordinate as a function of time for the same samples as shown in FIG. 2.

One procedure is to measure a component of the transient NMR voltage (identified as $v_w$) which is proportional to the hydrogen in the water. This voltage is shown in FIGS. 2 and 3 and can be measured after a specific delay. This delay in a typical instance is about 50 microseconds. This voltage can be observed in the NMR response after first permitting the voltage from the solid part of the sample to decay to a relative insignificant value. Recalling that ideally the relation time $T_{2w}$ is much greater than $T_{2s}$, this isolates the NMR output response if the measurement is observed at a time approximately three times greater than $T_{2s}$.

A separate measurement is taken and yields a signal which is identified as $v_t$ which is proportional to the total hydrogen in the detection volume. This voltage is the peak signal, normally occurring about 5 to 7 microseconds after the time starts, as exemplified in FIGS. 2 and 3. This is taken very quickly, substantially less than the interval $T_{2s}$. With these two values $v_t$ and $v_w$, the weight percent water is then yielded by equation 1:

$$\text{Percent water} = k \, (v_w/v_t) \quad (1)$$

As will be observed in the foregoing relationship, voltage $v_t$ is proportional to the sample weight while the voltage $v_w$ is proportional to the water weight. This procedure enables the water percent on weight basis to be obtained without weighing the sample.

An alternate approach to the measurement of percent moisture in a material depends on the manner in which the water is affiliated with the supportive material. The water may be held by different hygroscopic mechanisms. In this instance, the relaxation time $T_{2w}$ will vary as a function of the percent of water. The variation of relaxation time is typically noted in materials such as starch, flour and the like. In this instance, a calibration curve of relation time $T_{2w}$ as a function of weight percent water must be first obtained. From that, an NMR determination of $T_{2w}$ can then be converted to weight percent water. In that instance, no weight measurement is required.

An example of the differences in binding mechanism which hold water in a material (coal in this particular instance) is shown in FIG. 3. There, it will be observed that the transient NMR signal from FIG. 2 is graphed on a semilog scale. Attention is first directed to the first set of data which is the curved segment or portion 30. It is a straight line portion 30 which is joined to the straight line segment or portion 31. The two join at an inflection point 32. In the semilog presentation of this data, the inflection point is the intersection of the straight line segments 30 and 31. It will be observed that the two line segments have slopes which differ. This is indicative of a multi-component exponential curve. In general terms, the equation for the curve formed of segment portions 30 and 31 is given by the relationship of $Ae^{-kt}$ plus $Be^{-mt}$ where A and B are the vertical intercepts at $t=0$, and k and m are the time constants for the solid and the water.

This type of curve includes negative exponents which are a function of time. As time extends, the exponential function reduces the value towards zero. It will be understood that the exponential factor describing the curve portion 31 has a constant which reduces the term rapidly towards zero so that the curve portion 30 is the only term remaining in the equation as time extends significantly.

The curve 30 is for a low moisture coal, typically that coal responding at the curve 16 in FIG. 2. For a coal characterized by intermediate levels of moisture, the same material for the curve 17 shown in FIG. 2 is found at 33. The curve 34 is for the coal shown at 18 in FIG. 2. All three responses shown in FIG. 3 shown inflection points of the same general characterization. It is believed that the inflection points can be described by graphic methods exemplified herein. Alternative approaches for determination of the inflection points can be undertaken.

It is believed that the curves shown in FIG. 3 are representative of signals where hydrogen is in the water (held by the material) and also, hydrogen is in the compounds that comprise the material. Coal is primarily carbon. It additionally includes significant portions of hydrocarbon materials. The hydrocarbons are known as "volatile" materials. Additionally, there will be ash content, but it is not important for NMR response. The hydrogen in the hydrocarbons is a volatile in the coal which contributes to the NMR interrogation. Accordingly, it is held by a different binding mechanism and provides a different response $T_{2s}$. FIG. 3 sets forth, in representative fashion, the interplay between the two types of hydrogen found in the flowing material. Recall that hydrogen is both in the water and the flowing material. Equation 1, given earlier, is a sufficient approach for obtaining a measure of the percent of water.

Figure 4:
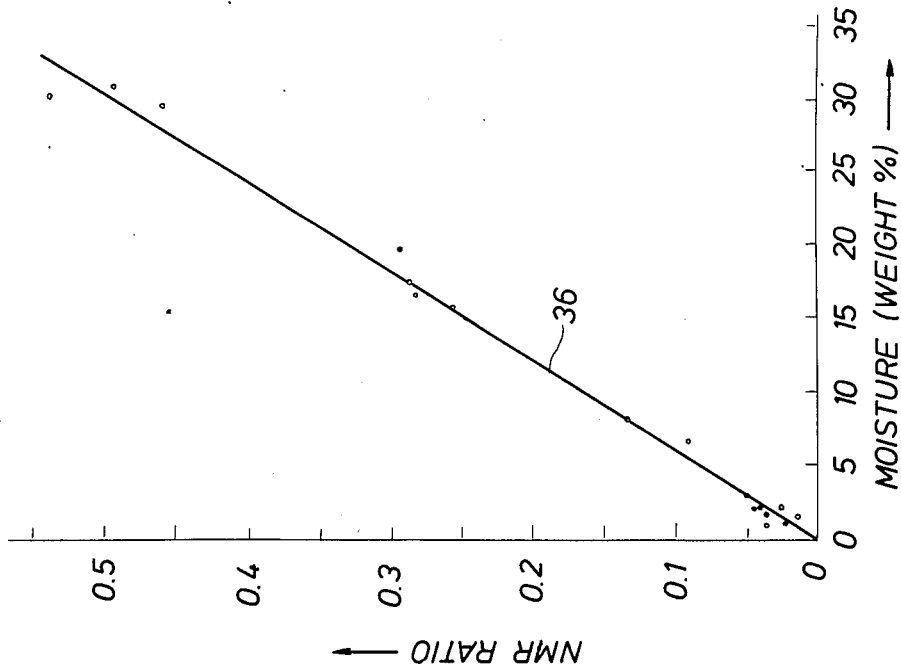
FIG. 4 is a graph of the ratio of transient NMR signals versus percent moisture for various samples of coal.

Attention is directed to FIG. 4 of the drawings where the data is presented in a different format. The ordinate is the ratio between the voltage proportional to the water and the sum of the voltages proportional to the water and the solid, or the ratio $v_w/(v_w+v_s)$. The curve 36 shows a fairly linear relationship between ratio and percent water. It has been found that the percent moisture is proportional to the ratio of the amplitude $v_w$ of the long relaxation time component extended so that it can be measured at the time of the peak value (about 5–7 microseconds) shown in FIG. 2 and divided by the amplitude of the peak value also measured at the peak shown in FIG. 2. This yields the ratio which is the ordinate in FIG. 4. This ratio, having been tested for 16 different samples of coal, yields the graph 36 shown in FIG. 4. For assay purposes, the percent water for the samples was determined gravimetrically. The straight line relationship for the selected samples had a confidence factor of 0.984, and a slope of 0.0217. In this particular arrangement, for this particular type of coal, this yielded a set of constants which is given in equation 2:

$$\text{Percent water} = 46 \text{ (NMR ratio)} \quad (2)$$

The volatiles in coal define a more rapidly decaying component of the output transient NMR signal. The percent of volatiles can be determined by a constant times the ratio of the peak of the transient NMR signal minus the water component signal measured at the same instant, all divided by the peak hydrogen signal. This is given in equation 3:

$$\text{Percent volatile} = K \left( \frac{V_P - V_W}{V_P} \right) \quad (3)$$

In the foregoing, the term $v_p$ equals the peak NMR signal and $v_w$ equals the value of the water component. If the type of coal does change (and hence the volatile mixture in the coal changes), the conversion constant k may not hold steady and may vary. Since the data graphed in FIG. 4 was taken from different types of coal, the variation in k with the type of coal should be small.

Figure 5:
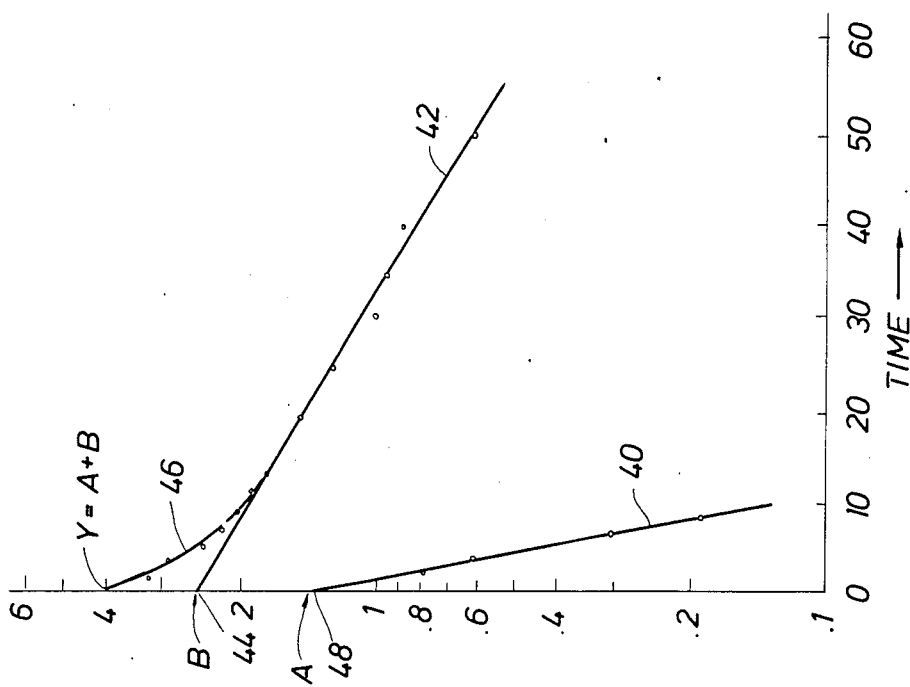
FIG. 5 is a graph of NMR signals separating a signal into components.

Attention is next directed to FIG. 5 of the drawings, which again, is a graph presented in a semilog scale. Briefly, there is a straight line segment 40 which is given by the form $Ae^{-kt}$. Again, the exponential relationship decays towards zero with the passage of time. The total signal is the sum of two such exponentials which add to define equation 4:

$$Ae^{-kt} + Be^{-mt} = \text{NMR response.} \quad (4)$$

Again, each term in this relationship approaches zero with the passage of time. The data shown in FIG. 5 is able to be evaluated by extending the straight line segments 40 and 42 to the intercept on the ordinate. The curve 42 has an intercept point at 44. When the curve 42 is extended to the intercept, it yields the value of the constant B shown in FIG. 5. The curve 42 is thus drawn with sufficient data points so that the straight line can be determined, and then the line is extended to the intercept 44 or the constant B. It will be observed that the curve deviates near time=zero, thereby disclosing the curve portion 46. This curve portion 46 results from the addition of the other term. So to speak, the curve portion 46 is the result of adding in a second term which describes the curve 40 to the terms described above. When the two straight line segment portions are added, they form the curve at 46. If the curve 42 can be determined along with its intercept 44 and if the curve 40 can be determined along the ordinate intercept 48, then the equation which describes the full set of data can be taken apart, being two straight line segments. One segment is the straight line portion 42 having the B intercept at 44. The second segment is the straight line portion 40 having the A intercepted at 48. The intercept 48 provides the second intercept value. The values determined at 44 and 48 are the constants B and A in equation 4 given above. The value of k in equation 4 comes from the slope of the line 40 from which the spin-spin relaxation time $T_{21} = 1/k$ is calculated. In similar fashion, the value of m in equation 4 comes from line slope, namely, the spin-spin relaxation time $T_{22} = 1/m$. The exponentials have characteristic values $T_{21}$ and $T_{23}$ which are determined by the nature of the binding mechanism for the hydrogen. For the water part, that is known at $T_{22}$. For a given assay of coal, that characteristic value is known also because the value of the binding mechanism which holds the hydrogen in the coal volatiles can be empirically measured as $T_{21}$. Typically, the volatiles are a mix of different paraffinic constituents. Again, when the assay of the coal is observed to change, the exponential factor may change with it.

This approach can be used for coal. It has also been successfully tested for other materials. The procedure is to take apart any hydrogen transient NMR curve, as described above, determining the two intercepts 42 and 48 and then the exponentials k and m which are constants A, B, k and m in equation 4; thereafter, record and store data calculated from the NMR response of a flowing material. Three and more curve segments may be included have been measured in various materials; they describe three or more intercepts which can be determined and three or more exponential time constants which can be determined in the same fashion.

Assume that the flowing material is coal. Assume further that the assay of the coal is known with a reasonable degree of accuracy so that the mix of volatiles in the coal is known. Percent of volatiles in the coal (contrasting the volatiles to the remaining carbon and ash material) is fairly well fixed. In this instance, all terms in equation 4 are then known. NMR data is then obtained from a specimen. By taking the data apart in the fashion described for FIG. 5, sufficient information is then obtained to thereby indicate the hydrogen population in water form. Sufficient data is also obtained to determine the hydrogen population in the coal volatiles and hence a measure in the quantity of coal. At this juncture, the percent of water in the flowing material can be determined without measuring the weight, this being simply the ratio of the voltage proportional to the number of hydrogen nuclei in water (from the water component intercept) to the voltage proportional to the number of nuclei in the coal (from the solid intercept)

plus the voltage proportional to the number of hydrogen nuclei in the water (from the water component intercept) all multiplied by a constant, kw.

From FIG. 5 and equation 4, the percent water is calculated from equation 5.

$$\text{Percent Water} = k_w B/(A+B), \quad (5)$$

and the percent volatiles is calculated from equation 6, $$\text{Percent Volatiles} = k_v A/(A+B). \quad (6)$$

While the foregoing is directed to the preferred embodiment, the scope is determined by the claims which follow.

What is claimed is:

1. A method of measuring moisture in a flowing material which moisture is subject to different bonding mechanisms as a function of percent water concentration comprising the steps of:
    (a) in a flowing material subject to interrogation, obtaining by a transient response a NMR response indicative of the total hydrogen population in an NMR detection volume for the flowing material;
    (b) plotting the transient NMR response as a function of time after interrogation;
    (c) extending selected portions of the plotted NMR response to an intercept at time equals zero to obtain intercept values A and B, the portions being selected to define at least two straight line segments;
    (d) determining K and M from the slope of the straight line portions of the plotted NMR response where K and M are characteristic for different water binding mechanisms in the flowing material; and
    (e) determining with the intercept values a moisture relationship for different water binding mechanisms given by $$Ae^{-kt} + Be^{-mt}.$$

2. The method of claim 1 wherein one term becomes insignificant compared to the other term as time increases.

3. The method of claim 1 including a third term $Ce^{-Nt}$ and C is an intercept value from extending a selected portion of the plotted NMR response to an intercept and N is the slope of a straight line portion of the plotted NMR response and is characteristic for a different water binding mechanism.

4. The method of claim 1 including the step of plotting on a semilog scale time dependent NMR response to define straight line portions, and extending the straight line portions to intercepts with the time at zero.

5. The method of claim 4 including the step of extending a straight line portion to an intercept through the largest time portions;
    thereafter subtracting the extended straight line portion extended to the intercept from the plotted data to isolate remaining straight line portions.

6. The method of claim 5 including the repeated steps of subtracting straight line portions beginning with the straight line portion determined by the largest time portions and then the straight line portion of the next largest time portions until all data for the shortest time portions has been determined.

7. A method of determining water absorbed in a flowing material which material includes hydrogen compounded in the material, the method comprising the steps of:
    (a) obtaining by NMR interrogation a first voltage proportional to the total hydrogen population in the material in the transient NMR detection volume having the flowing material therein;
    (b) separating the transient NMR response obtained by the first step into voltage components dependent on the hydrogen in the material $V_1$ and the hydrogen in the water $V_2$;
    (c) forming a ratio of the hydrogen related voltage components $V_2/(V_1+V_2)$; and
    (d) multiplying the ratio by a scale factor to obtain $KV_2/(V_1+V_2)$ which gives a measure of the moisture content in the flowing material.

8. The method of claim 7 including the step of separating the transient NMR signal as a function of the spin-spin relaxation times of hydrogen in the water $T_{22}$ and in the flowing material, $T_{21}$.

9. The method of claim 8 wherein the separation is dependent on $T_{22}$ being at least threefold times $T_{21}$ comparing the hydrogen in the absorbed water and in the flowing material.

10. The method of claim 8 wherein the separation is dependent on the relationship:

$$Ae^{-Kt} + Be^{-Mt}$$

where A and B are intercepts at time equal zero, and K and M are characteristic of the hydrogen in the water absorbed in the material and the hydrogen in the molecules of the flowing material which contains the absorbed water.

11. A method of measuring moisture in a static or flowing material of interest, the material having structurally bonded water of differing but unknown amounts wherein the measurement is taken by hydrogen transient NMR interrogation of water in a static or flowing material comprising the steps of
    (a) obtaining by hydrogen transient NMR interrogation a first voltage $V_1$ proportional to the hydrogen population in the NMR detection volume having a sample of the static or flowing material therein;
    (b) obtaining a standard voltage $V_s$ using the same hydrogen transient NMR system as for $V_1$ from a standard sample of the static or flowing material with known values of structurally bonded water concentration and a volume larger than the sensitive volume and a known weight of water $W_s$;
    (c) developing from the voltage $V_s$ and the weight of the water $W_s$ in the standard a conversion factor which is $W_s/V_s$ in weight unit per volt;
    (d) multiplying the first voltage $V_1$ by the conversion factor $W_s/V_s$ to obtain the value for the weight of water in the unknown static or flowing sample of material; and
    (e) converting the weight of the water to percent structurally bonded water in the unknown static or flowing sample by dividing the water weight $W_1$ by the weight of the unknown static or flowing sample.

12. The method of claim 11 for a flowing material including the step of measuring the peak amplitude of the hydrogen transient NMR signal for the first voltage and the peak amplitude of the hydrogen transient NMR signal obtained from the standard sample of known concentration of water, known volume and known weight in the same detection volume.

13. The method of claim 11 for a flowing material including the step of measuring the first voltage in an interval of time, while the material flows through the detection volume, which is short compared to the time of movement of the material through the sensitive volume.

14. The method of claim 11 for a flowing material wherein said NMR interrogation is obtained by pulse interrogation of a material flowing in a pipe.

15. The method of claim 14 wherein the pulse duration is sufficiently short in time that flow in the pipe does not disturb pulse interrogation.

16. The method of claim 15 wherein pulse interrogation involves a pulse in the range of up to about 20 microseconds.

17. The method of claim 11 for a flowing material wherein the NMR interrogation involves analysis of the hydrogen transient NMR to determine the $T_2$ values for each bonding phase of water which varies with water bonding mechanism and the water concentration in the flowing material.

18. A method of measuring moisture in a flow of coal, which coal contains differing amounts of bonded moisture and volatile components wherein the measure is taken by NMR interrogation of the flowing coal and the method comprises the steps of:
(a) obtaining by hydrogen transient NMR interrogation a signal indicative of the total hydrogen population in the NMR detection volume for the flowing coal and plotting the result in a semilog relationship;
(b) determining from the plotted semilog relationship total hydrogen transient NMR signal a peak value, which peak occurs at a time between about 5 and about 7 microseconds after time equals zero, and which peak is proportional to the number of hydrogen nuclei in the total sample in the detection volume and is labeled $V_t$;
(c) determining from the above total hydrogen transient NMR peak signal from the coal a voltage which occurs at about 20 microseconds which is proportional to the number of hydrogen nuclei bound into the coal and is called $V_w$;
(d) determining from the NMR response which is proportional to the bound water a measure of the hydrogen in the volatile components by subtracting $V_w$ from $V_t$ which is proportional to the bound water plus the volatiles;
(e) forming a ratio between the voltage proportional to the bound water $V_w$ and the voltage $V_t$ proportional to the total hydrogen in the sample in the detection volume; and
(f) multiplying the ratio $V_w/V_t$ by a scale factor K to obtain a measure of the moisture content in the flowing coal without weighing the sampled volume.

19. The method of claim 18 wherein the NMR response is given by the relationship of $Ae^{-Kt}+Be^{-Mt}$ wherein A and B are measured values, t is time, and K and M are measured characteristics for the hydrogen bound in the volatile components and water and A is obtained from the plotted semilog relationship curve fitting with a straight line projecting to time equals zero.

20. The method of claim 18 where the cool moisture concentration is measured in weight percent without weighing the sample.

21. The method of claim 18 wherein the step of determining the hydrogen population includes transmitting an RF pulse into the NMR detection volume; and observing the NMR response for an interval of time to obtain separable time dependent signal components therefrom.

22. The method of claim 18 wherein spin-spin relaxation time $T_2$ of the hydrogen is dependent on (1) the binding of the water and (2) the binding of the volatile components in the coal, and transient NMR output signal includes components dependent on $T_2$ of hydrogen in the water and volatile components and the values of $t_2$ are sufficiently different for the components, water and volatiles, can be separated.

* * * * *